United States Patent [19]

Fetter et al.

[11] Patent Number: 5,097,845

[45] Date of Patent: * Mar. 24, 1992

[54] MICROWAVE HYPERTHERMIA PROBE

[75] Inventors: Richard W. Fetter, Colgate; Peter D. Gadsby, Cedarburg, both of Wis.; Jeffery L. Kabachinski, Boynton Beach, Fla.

[73] Assignee: Labthermics Technologies, Champaign, Ill.

[*] Notice: The portion of the term of this patent subsequent to Jun. 27, 2006 has been disclaimed.

[21] Appl. No.: 547,535

[22] Filed: Jun. 29, 1990

Related U.S. Application Data

[62] Division of Ser. No. 371,202, Jun. 26, 1989, abandoned, which is a division of Ser. No. 108,923, Oct. 15, 1987, Pat. No. 4,841,988.

[51] Int. Cl.$^5$ ............................................. A61N 5/02
[52] U.S. Cl. .................................. 128/804; 128/784; 219/10.55 F
[58] Field of Search .................. 128/784, 401, 804; 219/10.55 A

[56] References Cited

U.S. PATENT DOCUMENTS

| | | | |
|---|---|---|---|
| 3,230,957 | 1/1966 | Seifert | 128/804 |
| 3,783,221 | 1/1974 | Soulier | 219/10.55 A |
| 4,316,474 | 2/1982 | Spethmann | 128/804 |
| 4,589,424 | 5/1986 | Vaguine | 128/804 |
| 4,643,186 | 2/1987 | Rosen et al. | |
| 4,700,716 | 10/1987 | Kasevich et al. | 128/804 |
| 4,813,429 | 3/1989 | Eshel et al. | |
| 4,825,880 | 5/1989 | Stauffer et al. | 128/804 |
| 4,841,988 | 7/1989 | Fetter et al. | 128/804 |

FOREIGN PATENT DOCUMENTS

| | | | |
|---|---|---|---|
| 1130534 | 5/1962 | Fed. Rep. of Germany | 128/804 |
| 1143938 | 2/1963 | Fed. Rep. of Germany | 128/804 |
| 1188490 | 4/1970 | United Kingdom | 128/804 |
| 1563795 | 5/1975 | United Kingdom | |
| 2045620A | 3/1979 | United Kingdom | |

OTHER PUBLICATIONS

Li et al., "Design . . . Microwave Applicator . . . ", *Int. J. Rad, Onc. Biol. Phys.*, vol. 10, pp. 2155–2162, Nov. 1984.

Wu et al., "Performance Characteristics . . . Hyperthermo", *Med. Phys.*, 14(2), Mar./Apr. 1987, pp. 235–237.

*Primary Examiner*—Lee S. Cohen
*Attorney, Agent, or Firm*—Reinhart, Boerner, Van Deuren, Norris & Rieselbach

[57] ABSTRACT

Heating pattern uniformity is provided in a coaxial microwave hyperthermia probe by varying the open area in the outer conductor in an axial direction such that there is a maximum open area in the axial center portion. The variations may be provided by winding an outer conductor in a helical pattern with a variable pitch or by cutting openings of axially varying size in a solid outer conductor. The invention is applicable to both flexible and rigid probes.

26 Claims, 1 Drawing Sheet

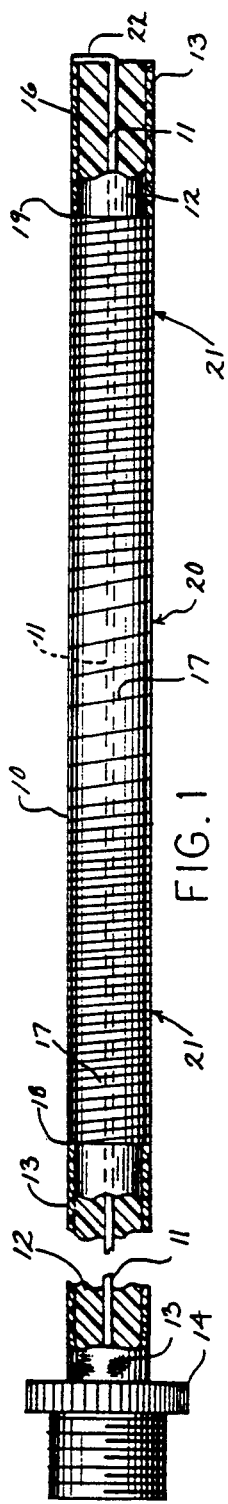
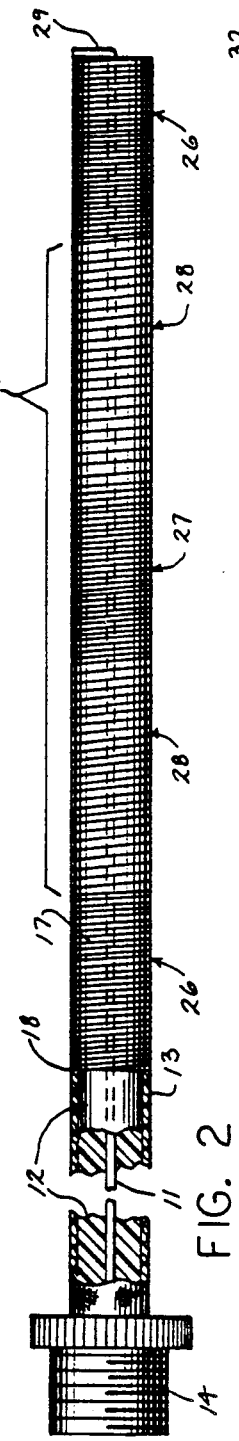
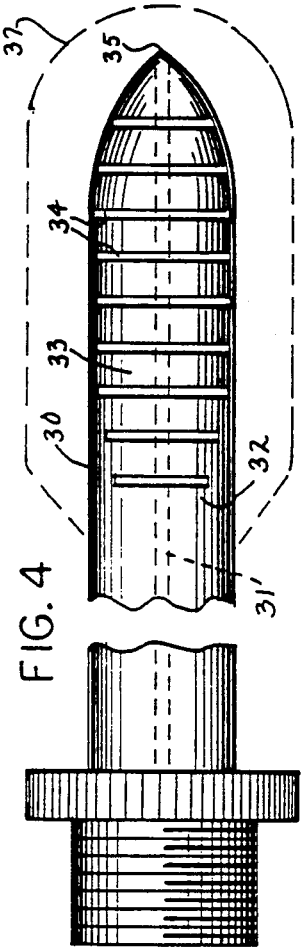
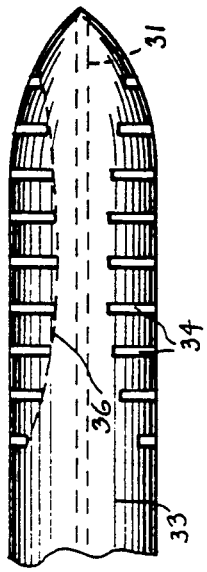
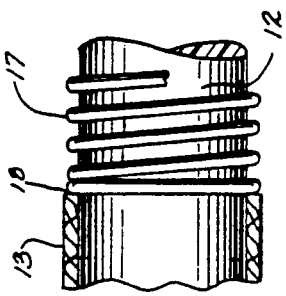
FIG. 1
FIG. 2
FIG. 3
FIG. 4
FIG. 5

MICROWAVE HYPERTHERMIA PROBE

This is a division of co-pending U.S. application Ser. No. 07/371,202 filed June 26, 1989, now abandoned, which in turn is a division of co-pending U.S. application Ser. No. 07/108,923, filed Oct. 15, 1987 by Richard W. Fetter, et al. now U.S. Pat. No. 4,841,988.

BACKGROUND OF THE INVENTION

The subject invention relates to microwave probes useful in hyperthermia therapy, and more particularly, to probes utilizing a coaxial antenna construction and useful primarily for the interstitial or invasive hyperthermia treatment of tumors.

It has long been known that certain cancer cells can be destroyed at elevated temperatures which are slightly lower than temperatures normally injurious to healthy cells. In recent years, hyperthermia therapy utilizing electromagnetic radiation has been found to be particularly effective and many processes and types of apparatus utilizing microwave hyperthermia are known in the art. These include non-invasive types in which external applicators are utilized and the microwave energy is allowed to penetrate the skin and underlying tissue, including a tumor to be treated. Obviously, this results in the heating of healthy tissue as well and this lack of control is one reason why more direct and exact means of applying microwave hyperthermia have been sought.

Thus, invasive methods and related apparatus have been developed in which a hyperthermia probe or probes may be inserted to the point of treatment via a normal body opening or may be inserted interstitially through the skin directly to the site of the tumor to be treated. Such invasive methods and apparatus provide the advantage of potentially better control of temperature of the mass or volume of tissue to be treated.

Since many types of malignancies cannot be reached and effectively treated with non-invasive techniques or with invasive probes designed to be inserted into a normal body opening, much attention has been recently given to long, narrow needle-like probes which can be inserted directly into the body tissue and to the site of the tumor or malignancy to be treated. Such probes must of necessity be of a very small diameter, both to aid the ease with which they may be inserted and used and to reduce the trauma associated therewith to the patient.

Interstitial microwave hyperthermia probes may be of a rigid or semi-rigid type with a needle-like point for direct insertion into the body tissue. Alternately, the probe may be more flexible and adapted to be used inside a catheter first inserted into the body tissue by ordinary, well-known methods. The advantages of using a probe inserted into a catheter include avoiding the need to separately sterilize the probe and to take advantage of catheters which may already have been inserted for other types of concurrent treatment, such as radiation therapy. Nevertheless, the convenience of more rigid probes adapted for direct interstitial insertion allow their alternative use in certain situations.

Regardless of the type of microwave probe, a problem common to all of them has been to provide a uniform pattern of radiated energy and heating axially along and radially around the effective length of the probe or to otherwise control and direct the heating pattern. A known and predictable heating pattern is, of course, important so that the heating may be confined to the greatest extent possible to the tissue to be treated and excessive heating of healthy tissue avoided.

Microwave probes of two kinds have been used, one comprising a monopole microwave antenna and the other a dipole coaxial antenna. In a monopole antenna probe, a single elongated microwave conductor is exposed at the end of the probe (sometimes surrounded by a dielectric sleeve) and the microwave energy radiates generally perpendicularly from the axis of the conductor. However, so-called monopole probes have been found to produce non-uniform and often unpredictable heating patterns and the heating pattern does not extend beyond the probe tip. As a result, more recent attention has been directed to so-called "dipole" antennas of a coaxial construction. These include constructions having an external reentrant coaxial "skirt" around the distal end of the outer conductor.

The typical coaxial probe includes a long, thin inner conductor extending along the axis of the probe, surrounded by a dielectric material, and an outer conductor surrounding the dielectric. To provide the effective outward radiation of energy or heating, a portion or portions of the outer conductor can be selectively removed. This type of construction is sometimes referred to as a "leaky waveguide" or "leaky coaxial" antenna. Obviously, variations in the location, size and area of the outer conductive material removed along the effective length of the probe can significantly affect the heating pattern provided. One of the primary goals in such construction has, thus, been to provide a uniform heating pattern generally or a more narrowly controlled and directed pattern in a selected region of the probe tip. U.S. Pat. No. 4,204,549 discloses the removal of short semi-cylindrical sections of the outer conductor in a coaxial probe to provide directional control of the heating pattern, but uniformity in the control of the heating pattern is not discussed. U.S. Pat. No. 4,669,475 discloses a coaxial antenna probe in which a full circumferential cylindrical portion of the outer conductor is removed over a selected intermediate axial length of the probe. However, the heating pattern per se is not disclosed or described, and the heating pattern of individual or multiply oriented probes is controlled by varying the microwave energy supplied to the probes. U.S. Pat. No. 4,658,836 discloses the removal of long axial segments of the outer conductor to provide full length heating. Control of the heating pattern is attained by varying the thickness of supplemental outer dielectric covering or by a unidirectional variation in the axial outer conductor segments. In an alternate embodiment, the outer conductor is attached in a uniform double spiral pattern to provide the necessary open space for radiation leakage. However, the utility of the spiral pattern is disclosed as providing the probe with flexibility and to provide relative rotation of the heating pattern along the probe length. Finally, the probe of this patent is intended particularly for insertion into a body passage or cavity and not direct interstitial insertion into body tissue.

Control of the heating pattern in coaxial probes for interstitial hyperthermia treatment continues to be a problem. It is important to be able to control and predict the heating pattern axially along the effective length of the probe. Because of the need to maintain the very small diameter of these probes, it is impractical to utilize heating pattern control means which increase the effective diameter, such as an outer dielectric layer.

Thus, any improved means of heating pattern control should be compatible with the typical constructions of interstitial probes, whether they be of the flexible or rigid type.

SUMMARY OF THE INVENTION

In accordance with the present invention, heating pattern uniformity is provided in a coaxial microwave probe, both radially and axially along its effective length, by varying the open area in the outer conductor axially along the effective length of the probe such that there is a maximum open area in the axial center portion and smaller open areas in both opposite directions.

In a preferred embodiment, the typical continuous outer conductor is removed or eliminated along substantially the full effective heating length of the probe and replaced with a spiral winding of a conductive wire in which the winding has a varied spacing to provide the varying open area in the outer conductor. An extremely broad range of winding patterns may be used depending on specific probe construction characteristics. Typically, the effective length of the probe is divided into sections of different winding pitch. The sections may provide an overall symmetrical pattern or be asymmetric, the pitch within a section may be uniform or varying, transitioned pitch sections may be provided between the major sections, and each section itself may comprise subsections with variations in the windings.

In an alternate embodiment particularly applicable to rigid or semi-rigid probes in which the outer conductor is typically a thin solid metal covering, the axially varying open area in the outer conductor is attained by providing a series of axially spaced slots of varying length and depth. The slots are preferably transversely disposed in axially spaced planes perpendicular to the axis of the probe. As with the spirally wound embodiment, the slots are sized or spaced to provide a maximum open area in the center portion of the effective length of the probe and relatively smaller open areas axially in both directions therefrom. The slot pattern may be symmetrical or asymmetric in an axial direction, and may be otherwise varied in manner similar to the spirally wound embodiment.

The general arrangement of both embodiments has been found to provide the desired uniformity in the heating pattern, both radially and axially along the probe. In both embodiments, heating extends beyond the tip.

BRIEF DESCRIPTION OF THE DRAWING

FIG. 1 is a longitudinal view, partly in section, of the embodiment of the invention particularly adaptable for use with flexible coaxial probes.

FIG. 2 is a view similar to FIG. 1 showing a pattern in the wound outer conductor particularly suitable for longer probes.

FIG. 3 is an enlarged detail of a portion of the probe shown in FIG. 1.

FIG. 4 is a side view of a probe of a more rigid construction showing an alternate embodiment of the invention.

FIG. 5 is a top view of the probe shown in FIG. 4.

DETAILED DESCRIPTION OF THE PREFERRED EMBODIMENT

Referring to FIG. 1, a microwave probe 10 is constructed from a section of conventional small diameter flexible coaxial cable. The cable includes a wire-like center conductor which runs axially along the length of the cable and is surrounded by a cylindrical layer of suitable dielectric material 12. Many types of dielectrics are usable and a plastic material, such as PTFE, is often used. The dielectric material is, in turn, surrounded by an outer conductor 13 comprising a braided metal construction. Both the unitary center conductor 11 and the braided wire outer conductor 13 may be made of a copper base metal which is preferably silver-plated to enhance conductivity. Other suitable metals may, of course, also be used. The proximal end of the probe 10 includes a standard coaxial connector 14 for connection to a conventional source of microwave energy (not shown).

The conventional coaxial cable thus far described is modified to provide the present invention by removing a cylindrical section of the braided outer conductor 13 along the distal end of the probe. The axial length of the section of the outer conductor removed determines the effective length of the probe from the standpoint of the length along which an effective heating pattern may be produced. A short section of braided outer conductor 16 may be left at the probe tip to facilitate the conductive connections to be hereinafter described, but that short section may be eliminated as well and the conductive connections made in another manner.

In place of the section of the braided outer conductor 13 removed from the end of the cable, a thin wire 17 is wound in a helical pattern over the dielectric 12 and between the outer conductor 13 at the proximal end of the probe to the free end thereof. Referring also to FIG. 3, appropriate conductive connections 18 and 19 are made between the wire 17 and the ends of the outer conductor 13 between which the spiral winding is made. Alternately, if the short section of outer conductor 16 at the end of the probe is eliminated, the spiral winding is simply run to the probe tip.

In a specific embodiment of the probe shown in FIG. 1, which may have an effective length (or axial heating pattern length) of about 4 cm (approximately 1.5 inches), the center conductor 11 has a diameter of 0.007 inch. The cylindrical dielectric covering 12 has an outer diameter of 0.033 inch and the braided outer conductor is about 0.010 inch in thickness. The conductive wire winding 17 is 0.007 inches in diameter. Thus, the nominal OD of the probe along its effective length is 0.047 inch.

The spiral winding pattern shown includes a center portion 20 and end portions 21 adjacent thereto. The wire 17 is preferably wound with a spaced pitch over the full length of the winding and with the maximum spacing in the center portion 20 to provide the maximum open area in the outer conductor for microwave energy leakage or radiation. In the probe shown, the center portion 20 has a length of about 0.250 inch and the end portions 21 lengths of 0.295 inch each. The spaced pitch of the winding of wire 17 in the center portion 20 is 0.0281 inch and the spaced pitch of the end portions 21 is 0.0095 inch. Suitable pitch transition zones may be provided between the portions 20 and 21.

The actual heating pattern provided by the probe extends axially in both directions beyond the conductive connection 18 and 19 between the wire 17 and the outer conductor 13. Typically, the heating pattern will extend about 0.2 inch (0.5 cm) beyond the tip of the probe. Thus, the effective heating pattern provided by the probe is approximately 4 cm.

FIG. 2 shows an alternate embodiment of the spirally wound probe shown in FIG. 1, adapted particularly for longer probe constructions. Overall, the components of the probe 23 in FIG. 2 are the same as those in the embodiment of FIG. 1 and are, therefore, identically numbered. Thus, a conventional coaxial cable has a conductive inner member 11, surrounded by a dielectric 12, and around which is disposed an outer conductor 13. The outer conductor, which may be of the braided construction previously described, is cut away to expose the dielectric material 12 at the end of the probe 23.

Beginning with a conductive connection 18 to the end of the outer conductor 13, a wire 12 is wound in a helical pattern which, in this embodiment, runs to the end of the probe. The wire is wound in a spaced arrangement and the pitch of the winding varies over the length of the probe with a maximum spaced pitch in the center portion. However, in this embodiment, the center portion 24 of the winding itself comprises a winding having a variable spaced pitch.

In the specific construction shown, the center portion 24 of the winding includes a narrowly spaced center subportion 27 and more widely spaced end subportions 28 either side. The end portions 26 again comprise a winding of a narrow spaced pitch. In one preferred construction, the end portions 26 each have a length of 0.472 inch and are wound to a pitch of 0.0169 inch. The center end subportions 28 are each 0.689 inch in length and are wound to a pitch of 0.0276 inch each. The center subportion 27 is identical to the end portions 26 having a length of 0.472 inch and a pitch of 0.0169 inch.

The effective heating pattern of the FIG. 2 probe is approximately 8 cm or slightly greater than 3 inches. The heating pattern also has uniform radial depth along substantially its entire length. Depending on the power level of the microwave energy supplied to the probe, the uniform heating pattern may extend radially for a centimeter or more. The axial extension of the heating pattern toward the proximal end of the probe over a short portion of the braided outer conductor 13 allows a thermocouple to be located at that point. In this manner, the thermocouple or other heat sensor connections will not interfere with the operation of the probe and yet are attached in an area where the measured temperature is representative of that effectively applied by the probe.

Referring now to FIGS. 4 and 5, there is shown an alternate embodiment of the probe which is of a rigid or semi-rigid construction and intended for direct insertion into body tissue without the use of a catheter. The probe 30 is of a basic coaxial construction, including an axial inner conductive member 31, a dielectric material 32 surrounding the inner conductor, and a conductive outer shell or layer 33. To provide the desired pattern of heating to extend beyond the tip of the probe, the outer conductive layer 33 is suitably formed to a point and makes conductive contact 35 with the inner conductor 31 at the tip of the probe.

To provide the axially varying open area in the outer conductive layer 33, a series of transverse slots 34 is cut into the outer layer 33 and underlying dielectric material 32 on diametrically opposite sides of the probe 30. The slots 34 are of maximum length and depth in the center portion of the axially disposed slot pattern and become progressively smaller in both axial directions therefrom. The deepest centrally located slot or slots may have a maximum depth of approximately ⅓ the diameter of the probe and the receding depths of the slots in opposite axial directions should preferably fit a smooth curve, as shown by the dashed line 36 in FIG. 5.

The rigid probe 30, in a preferred embodiment, has an outer diameter of 0.086 inch. The slot pattern comprises nine slots 34 spaced at 0.25 inch with the small slot nearest the tip spaced 0.375 inch therefrom. The foregoing dimensions, however, may be varied over fairly broad ranges. In order to provide a smooth outer surface on the probe and to better match the probe impedance to the tissue in which it is intended to be used, the slots are filled with a material having a high dielectric constant, such as titanium dioxide.

The dashed line 37 in FIG. 4 is representative of the uniform heating pattern attained with each embodiment of the hyperthermia probe of the subject invention. Each embodiment described hereinabove includes an axially symmetrical pattern around the opening provided in the outer conductor. Such symmetry, though desirable, is not necessary and variation including asymmetrical patterns in the openings may also be used to provide the desired heating pattern.

Various modes of carrying out the invention are contemplated as being within the scope of the following claims particularly pointing out and distinctly claiming the subject matter which is regarded as the invention.

I claim:

1. In a coaxial microwave probe for interstitial hyperthermia treatment having a conductive inner member extending axially along the length of the probe, a dielectric material surrounding the inner member along substantially its full length, and an outer conductive member surrounding the dielectric material, said outer conductive member having a generally open area defining an effective heating length of the probe to provide a desired heating pattern, the improvement comprising said outer conductive member disposed in a helical pattern along the effective length, said helical pattern defining a variable spaced pitch to provide a maximum open area in the center portion of the effective length and smaller open areas axially in both directions therefrom.

2. The invention as set forth in claim 1 wherein the outer conductor comprises a wire.

3. The invention as set forth in claim 2 wherein the probe has a substantially uniform cylindrical outer diameter.

4. The invention as set forth in claim 3 wherein the pitch of the helical pattern varies within a range of about 25% to 85% of the outer diameter of the probe.

5. The invention as set forth in claim 3 wherein the helical pattern comprises a large pitch center portion and relatively smaller pitch portions adjacent thereto.

6. The invention as set forth in claim 5 wherein the helical pattern is symmetrical along the probe axis.

7. The invention as set forth in claim 5 wherein the center portion comprises a helical pattern having a variable spaced pitch.

8. The invention as set forth in claim 3 including a probe tip and wherein the inner member is conductively attached to the outer member at the probe tip.

9. In coaxial microwave probe for interstitial hyperthermia treatment having a conductive inner member extending axially along the length of the probe, a dielectric material surrounding the inner member along substantially its full length, and an outer conductive member surrounding the dielectric material, said outer conductive member having a generally open area defining an effective heating length of the probe to provide a desired heating pattern, the improvement wherein said outer conductive member comprises a narrow conductor disposed in a helical pattern along the effective length of the probe with the pitch of said helical pattern varying along the effective length.

10. The invention as set forth in claim 9 wherein the helical pattern comprises at least two axially adjacent portions each having a different pitch.

11. The invention as set forth in claim 10 wherein the outer conductor member comprises a continuously wound wire.

12. The invention as set forth in claim 11 wherein the probe is laterally flexible.

13. The invention as set forth in claim 9 wherein the helical pattern comprises at least three portions.

14. The invention as set forth in claim 13 wherein two of said portions have a substantially equal pitch.

15. The invention as set forth in claim 14 wherein the third portion is disposed between said two equal pitch portions.

16. In a coaxial microwave probe for interstitial hyperthermia treatment having a conductive inner member extending axially along the length of the probe, a dielectric material surrounding the inner member along substantially its full length, and an outer conductive member surrounding the dielectric material, said outer conductive member having a generally open area defining an effective heating length of the probe to provide a desired heating pattern, the improvement comprising said outer conductive member formed from a wire wound in a helical pattern of axially varying pitch.

17. The invention as set forth in claim 16 wherein said helical pattern comprises axially adjacent portions of different pitch.

18. A coaxial microwave probe for interstitial hyperthermia treatment comprising:
an elongate conductive inner member;
a dielectric material surrounding said inner member;
an outer conductive member surrounding said dielectric material, said outer conductive member having a generally open area defining an effective heating length of the probe; and
a helical conductive member disposed around said open area along said effective heating length, said helical conductive member having one end electrically connected to said outer conductive member and another end electrically connected to said inner conductive member, said helical conductive member further having an axially varying pitch.

19. A coaxial microwave probe as set forth in claim 18 wherein said helical conductive member comprises a wire spiral winding.

20. A coaxial microwave probe as set forth in claim 19 wherein said probe has a substantially uniform cylindrical outer diameter.

21. A coaxial microwave probe as set forth in claim 20 wherein the pitch of said helical conductive member varies within a range of about 25% to 85% of the outer diameter of said probe.

22. A coaxial microwave probe as defined in claim 20 wherein said helical conductive member includes a center portion of relatively large pitch and portions of relatively smaller pitch adjacent said center portion.

23. A coaxial microwave probe as set forth in claim 22 wherein said helical conductive member is symmetrical along the probe axis.

24. A coaxial microwave probe as set forth in claim 23 wherein said center portion has a variable-spaced pitch.

25. In a coaxial microwave probe for treatment of abnormal bodily tissues having a conductive inner member extending axially along the length of the probe, a dielectric material disposed about the inner member along substantially its full length, and an outer conductive member disposed about said dielectric material, said outer conductive member at least in part defining a desired heating pattern, the improvement comprising said outer conductive member formed from a wire wound in a helical pattern of axially varying pitch.

26. The invention as set forth in claim 25 wherein said helical pattern comprises axially adjacent portions of different pitch.

* * * * *